(12) United States Patent
McElroy

(10) Patent No.: US 10,036,700 B2
(45) Date of Patent: Jul. 31, 2018

(54) SIMULATION TOOL FOR DAMAGE IN COMPOSITE LAMINATES

(71) Applicant: The United States of America, as represented by the Administrator of the National Aeronautics and Space Administration, Washington, DC (US)

(72) Inventor: Mark W. McElroy, Houston, TX (US)

(73) Assignee: THE UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 0 days.

(21) Appl. No.: 15/526,369

(22) PCT Filed: Oct. 1, 2015

(86) PCT No.: PCT/US2015/053459
§ 371 (c)(1),
(2) Date: May 12, 2017

(87) PCT Pub. No.: WO2016/076965
PCT Pub. Date: May 19, 2016

(65) Prior Publication Data
US 2017/0322145 A1  Nov. 9, 2017

Related U.S. Application Data

(60) Provisional application No. 62/079,182, filed on Nov. 13, 2014, provisional application No. 62/087,841, filed on Dec. 5, 2014, provisional application No. 62/166,319, filed on May 26, 2015.

(51) Int. Cl.
*G01N 19/08* (2006.01)
*G01N 3/00* (2006.01)

(52) U.S. Cl.
CPC ............... *G01N 19/08* (2013.01); *G01N 3/00* (2013.01); *G01N 2203/0025* (2013.01); *G01N 2203/0066* (2013.01); *G01N 2203/0212* (2013.01); *G01N 2203/0216* (2013.01)

(58) Field of Classification Search
CPC .. G01N 19/08; G01N 3/00; G01N 2203/0025; G01N 2203/0066; G01N 2203/0212; G01N 2203/0216
USPC ............................................ 73/799
See application file for complete search history.

(56) References Cited

U.S. PATENT DOCUMENTS

| 2002/0112548 | A1* | 8/2002 | Dong | ..................... B23K 31/02 |
| | | | | 73/850 |
| 2004/0148143 | A1 | 7/2004 | Deobald et al. | |
| 2006/0009951 | A1 | 1/2006 | Tryon et al. | |
| 2008/0172211 | A1 | 7/2008 | Sakai et al. | |

(Continued)

OTHER PUBLICATIONS

PCT International Search Authority and Written Opinion, PCT/US2015/53459, dated Dec, 28, 2015, 10 pages.

*Primary Examiner* — Max Noori
(74) *Attorney, Agent, or Firm* — Andrea Z. Warmbier; Robin W. Edwards; Mark P. Dvorscak

(57) ABSTRACT

A numerical simulation tool for progressive failure in laminates utilizes a low fidelity approach. The numerical model includes an enriched element that is initially in a low fidelity form. The enriched elements may increase fidelity by splitting locally to simulate an ongoing damage process such as delamination.

20 Claims, 8 Drawing Sheets

(56) References Cited

U.S. PATENT DOCUMENTS

| | | | |
|---|---|---|---|
| 2012/0265449 A1* | 10/2012 | Ihn | G01N 27/026 |
| | | | 702/33 |
| 2014/0197848 A1* | 7/2014 | Gregoire | G01N 3/00 |
| | | | 324/637 |
| 2014/0278291 A1 | 9/2014 | Zheng et al. | |
| 2015/0082855 A1* | 3/2015 | Fujii | G06F 17/5018 |
| | | | 72/379.2 |
| 2016/0162616 A1* | 6/2016 | Hasan | G06F 17/5018 |
| | | | 703/2 |
| 2017/0219471 A1* | 8/2017 | Fisk | G01N 3/08 |

* cited by examiner

SIMULATION TOOL FOR DAMAGE IN COMPOSITE LAMINATES

CROSS-REFERENCE TO RELATED PATENT APPLICATIONS

This patent application claims the benefit of and priority to U.S. Provisional Patent Application No. 62/166,319, titled "SIMULATION TOOL FOR DAMAGE IN COMPOSITE LAMINATES" filed on May 26, 2015; U.S. Provisional Patent Application No. 62/087,841, titled "SIMULATION TOOL FOR DAMAGE IN COMPOSITE LAMINATES" filed on Dec. 5, 2014; and U.S. Provisional Patent Application No. 62/079,182, titled "SIMULATION TOOL FOR DAMAGE IN COMPOSITE LAMINATES" filed on Nov. 13, 2014. The entire contents of each of the above-identified provisional applications are hereby incorporated by reference in their entirety.

STATEMENT REGARDING FEDERALLY SPONSORED RESEARCH OR DEVELOPMENT

The invention described herein was made by an employee of the United States Government and may be manufactured and used by or for the Government of the United States of America for governmental purposes without the payment of any royalties thereon or therefore.

BACKGROUND OF THE INVENTION

Damage processes in laminates can be inherently complex. As a result, prior methods to simulate damage in composite laminates rely on high fidelity numerical (i.e., finite element) models. A primary disadvantage of prior high fidelity simulation models is that they can be cost inhibitive in terms of required user expertise, model development time, and computational resources. Often existing tools are not feasible for use outside of research or academic type environments because, even for consideration of a simple damage process in small structures, their use requires a high level of training and time. Furthermore, if a model becomes too high fidelity and involves too many interacting damage processes, there are more sources for error to appear and magnify. There are ways to mitigate these disadvantages such as dividing models of complex structures into component level models, or locally refining fidelity around the expected area of damage. However, in doing this, additional time and expertise is required, knowledge of expected behavior beforehand is required, and the model results can be influenced by the model creator. Difficulties associated with high fidelity models could be overcome if an accurate lower-fidelity simulation tool was available.

Accordingly, there is a need for a tool to simulate damage processes in composite laminates that is rapid and less demanding in terms of user expertise, model development time and computational resources, but of equal or similar accuracy and as a higher fidelity model.

BRIEF SUMMARY OF THE INVENTION

One aspect of the present invention is a numerical simulation tool for progressive damage in laminates. The simulation tool may utilize several numerical techniques (i.e., Floating Node Method (FNM), Virtual Crack Closure Technique (VCCT), finite element analysis) in connection with a developmental damage simulation theory in a manner necessary to fully capture the formation of a three dimensional internal crack network in a laminate using a model composed of a low fidelity mesh of planar type finite elements (i.e., a shell element, a plate element, or similar finite element). Shell/plate elements are general in nature, easily usable, and computationally efficient. The model mesh remains low fidelity throughout an analysis and increases in fidelity only locally as needed to suit a damage process occurring throughout a solution procedure.

The tool can be used to simulate three dimensional laminate damage processes and is in the form of an enriched shell finite element. One component of the tool includes numerical representation in a finite element mesh of material and structural discontinuities that can change/evolve according to an ongoing damage process using a discrete type modeling approach. One embodiment of this type of modeling approach includes a technique disclosed in "The Floating Node Method (FNM)," as described in Chen, B Y, S. T. Pinho, N. V. De Carvalho, P. M. Baiz, T. E. Tay, 2014, "A floating node method for the modeling of discontinuities in composites," Engineering Fracture Mechanics 127:104-134, which is hereby incorporated by reference in its entirety.

The tool includes a criteria to predict delamination growth. This may utilize the Virtual Crack Closure Technique (VCCT). A summary of this approach is described in Krueger, R. 2004, "Virtual crack closure technique: History, approach, and applications, Applied Mechanics Review," (57) 2:109-143, which is hereby incorporated by reference in its entirety.

The tool may also include a criteria to predict delamination migration in the form of matrix cracks internal to a laminate. In one embodiment, no details of this damage feature are simulated other than its location and occurrence. Details regarding investigation of a delamination migration criteria are disclosed in Ratcliffe, J. G., M. W. Czabaj, T. K. Obrien, 2013, "A test for characterizing delamination migration in carbon/epoxy tape laminates," NASA/TM-2013-218028, Canturri, C., E. S. Greenhalgh, S. T. Pinho, J. Ankersen, 2013, "Delamination growth directionality and the subsequent migration process: The key to damage tolerant design, Composites Part A: Applied Science and Manufacturing," (54):79-87 and Greenhalgh, E. S., Rogers, C., Robinson, P. "Fractographic observations on delamination growth and the subsequent migration through the laminate," Composites Science and Technology, 2009, 69:2345-2351, which are hereby incorporated by reference in their entirety.

The tool may also include a feature that numerically represents a geometric material discontinuity in the form of a transverse matrix crack that is adjacent to a delamination. A transverse matrix crack adjacent to a delamination may be represented in the finite element mesh as a discontinuity in mesh stiffness along an element boundary (i.e., in the case where a delamination migrates via a transverse matrix crack the laminate material on either side of the delamination changes in thickness at the migration location).

The enriched element is based on the formulation of a shear deformable shell/plate element. Suitable elements may be developed as user defined subroutines with commercial software ABAQUS, but the element could be developed using other suitable finite element software tools.

The invention may be utilized to simulate damage in composite laminate structures in various applications, including the fields of aerospace, automobile and marine industries. The invention may be useful for a structure design and certification by simulating impact damage, compression after impact damage, or any similar delamination driven damage process in a laminate. For example, the simulation tool of the present invention may be utilized to evaluate various composite laminates. A structural component for an aircraft, vehicle, space craft, ship, etc. may be designed based, at least in part, on the results provided by the simulation tool. More specifically, a composite laminate having acceptable resistance to damage (delamination matrix cracking, etc.) may be selected for a structural component of an aircraft or other vehicle using the simulation tool of the present invention, and a composite laminate having a ply orientation etc. as evaluated/selected using the simulation tool may be utilized in fabricating the component. The simulation tool of the present invention may reduce the need to fabricate and test various laminates during the design process, and also utilizes significantly less computer resources than prior multi-layer finite element methods utilized for damage simulation/evaluation of composite materials.

DETAILED DESCRIPTION OF THE INVENTION

Figure 1:
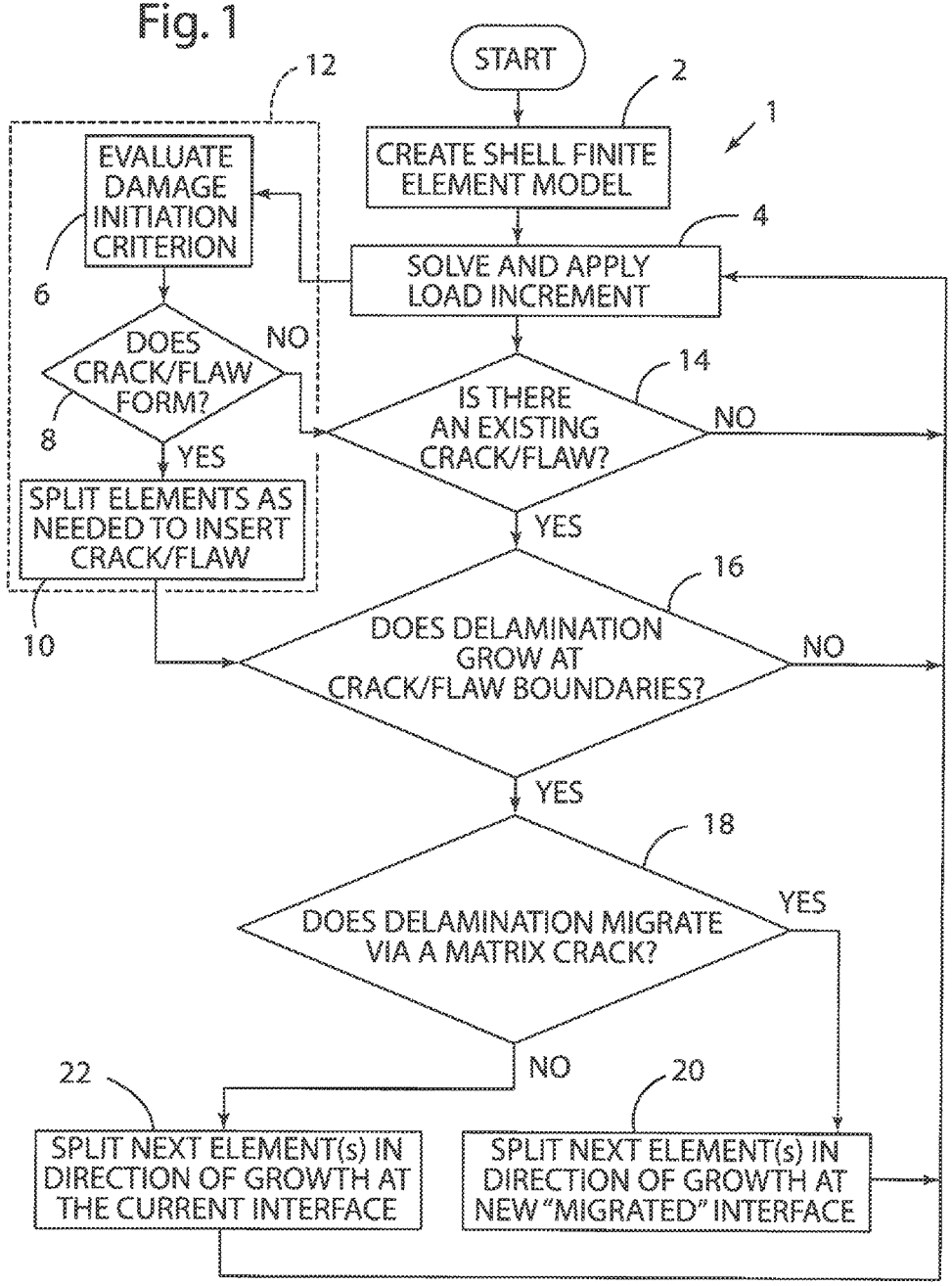
FIG. 1 is a flow chart showing a process of simulating damage in composite laminates according to one aspect of the present invention.
Figure 2:
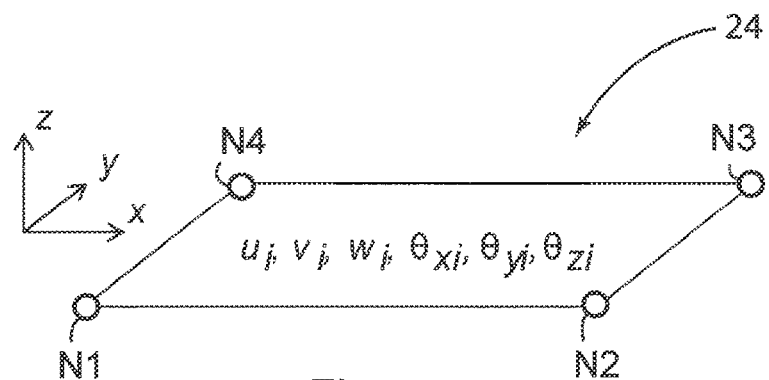
FIG. 2 is a schematic view showing a Mindlin composite shell element.

For purposes of description herein, the terms "upper," "lower," "right," "left," "rear," "front," "vertical," "horizontal," "positive," "negative," and derivatives thereof shall relate to the invention as oriented in FIG. 2. A summary of the process is shown in FIG. 1. However, it is to be understood that the invention may assume various alternative orientations and step sequences, except where expressly specified to the contrary. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

FIG. 1 depicts a process 1 according to one aspect the present invention. Following the start of process 1, a shell finite element model is created at step 2 and a load is applied. As discussed in more detail below, the shell finite element model is initially a model with a low-fidelity mesh including a plurality of adjacent (side-by-side, not "stacked") shell elements. The shell elements include a stiffness matrix corresponding to a composite laminate having a plurality of layers of fibers and a matrix material. The shell finite element model may initially include a single layer mesh composed of a plurality of single-layer shell elements with "floating" nodes that permit the shell element to be split as required to simulate delamination and delamination-matrix crack interaction. As used herein, the term "shell" generally refers to any finite element (e.g. shell, plate, etc.) capable of numerically modeling damage propagation in composite laminates as described herein. It will be understood that the present invention is not limited to shell elements.

Referring again to FIG. 1, at a next step 4, a load increment is solved. The process 1 may then proceed directly to step 14 (discussed below), or the process may proceed to optional steps or features shown in the dashed region 12. As discussed in more detail below, the optional process features relate to determining if a crack or flaw forms, and includes evaluating damage initiation criterion 6 throughout the model. This is followed by determining if a crack or flaw is formed at step 8. If a crack or flaw does form the shell elements are split as needed (preferably only as needed) to insert the crack or flaw at step 10, and the process proceeds to step 16. If no crack or flaw is formed at step 8, the optional processes proceeds to step 14. At 14, the process involves determining if there is an existing crack or flaw. If not, the process returns to 4, and the next load increment is solved. However, if it is determined at step 14 that there is an existing crack or flaw, the process proceeds to step 16. As discussed in more detail below, predefined criteria may be utilized to determine if a delamination grows at the crack or flaw boundary. If not, the process returns to 4, and the next load increment is solved. If the delamination does grow, the process then involves determining if the delamination migrates via a matrix crack at step 18. If the delamination crack does migrate, the next elements in the direction of the growth are split at a new interface as indicated at step 20, and the process then continues with the next load increment/solution 4. As discussed in more detail below, the stiffness matrices of the laminate at the migrated interface are not equal to the stiffness matrices at the prior interface to thereby account for the migration of the delamination crack via a matrix crack in the mesh at the element boundary.

If a delamination does not migrate at 18, the process continues as shown at 22. At 22, the next elements are split in the direction of growth at the current interface, and the process continues with the next load increment/solution 4. It will be understood that the process includes checking if the solution is complete after 20 and 22, and ending the process if the solution is complete. If the solution is not complete after 20 or 22, the process returns to 4 as shown in FIG. 1. It will be understood that the present invention is not necessarily limited to the steps and sequences described above in connection with FIG. 1. In general, there may be additional steps not shown in FIG. 1 following steps 20 and 22 for scenarios including: 1) when multiple delaminations interact with one another and may or may not link together via matrix cracks; and 2) an element that has migration predicted in one region but not in another in the same load increment.

With further reference to FIG. 2, a Mindlin composite shell element includes 4 nodes N1-N4. The stiffness matrix integration can be expressed utilizing the following general shell element stiffness integration equation:

$$K^{(e)} = \int_x \int_y H^T \left[ \int_z C dz \right] H\, dy\, dx = \int_b \int_b H^T \left[ \int_{-\frac{h}{2}}^{\frac{h}{2}} C dz \right] H\, dy\, dx \quad (1.0)$$

where:
H=strain-displacement matrix
C=constitutive material matrix
b=edge dimension of an element
h=total thickness of the laminate The laminate theory constitutive material matrices are as follows:

$$A = \int_{-\frac{h}{2}}^{\frac{h}{2}} C_p dz, \quad B = \int_{-\frac{h}{2}}^{\frac{h}{2}} z C_p dz \quad (2.0)$$

$$D = \int_{-\frac{h}{2}}^{\frac{h}{2}} z^2 C_p dz, \quad G = \int_{-\frac{h}{2}}^{\frac{h}{2}} C_s dz$$

wherein $C_p$ and $C_s$=planar and shear constitutive material matrices.

The laminate shell element stiffness integration is as follows:

$$K^{(e)} = \int_b \int_b H^T \left[ \int_{-\frac{h}{2}}^{\frac{h}{2}} C(A, B, D, G) dz \right] H\, dy\, dx \quad (3.0)$$

When a discontinuity is introduced at a single uniform z-coordinate, as in the case of a delamination, the element material is split into two regions, $\Omega_A$ and $\Omega_B$, where region $\Omega_B$ corresponds to the DOF of the floating nodes. The stiffness matrix for a split element is given by:

$$K^{(e)} = K_{\Omega_A}^{(e)} + K_{\Omega_B}^{(e)} \quad (4.0)$$

Figure 3:
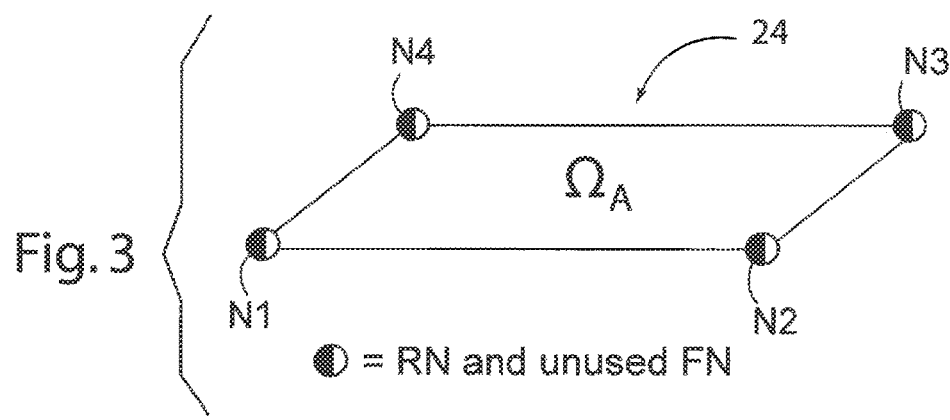
FIG. 3 is a schematic view of an undamaged shell element.

With further reference to FIG. 3, an undamaged shell element 24 initially includes nodes N1-N4 that comprise real nodes (RN) and unused floating nodes (FN). Floating nodes and real nodes are generally known in the art (see, Chen, "The Floating Node Method (FNM)" supra) Thus, a detailed description of these terms is not believed to be required.

The stiffness matrix for the undamaged shell element 24 is given by:

$$K^{(e)} = \begin{bmatrix} [K_{\Omega_A}^{(e)}]_{24 \times 24} & [0] \\ [0] & [0]_{24 \times 24} \end{bmatrix}_{48 \times 48} \quad (5.0)$$

The configuration of equation 5.0 allows for one delamination. However, it will be understood that the same approach may be utilized to allow for additional delaminations if required.

Figure 4:
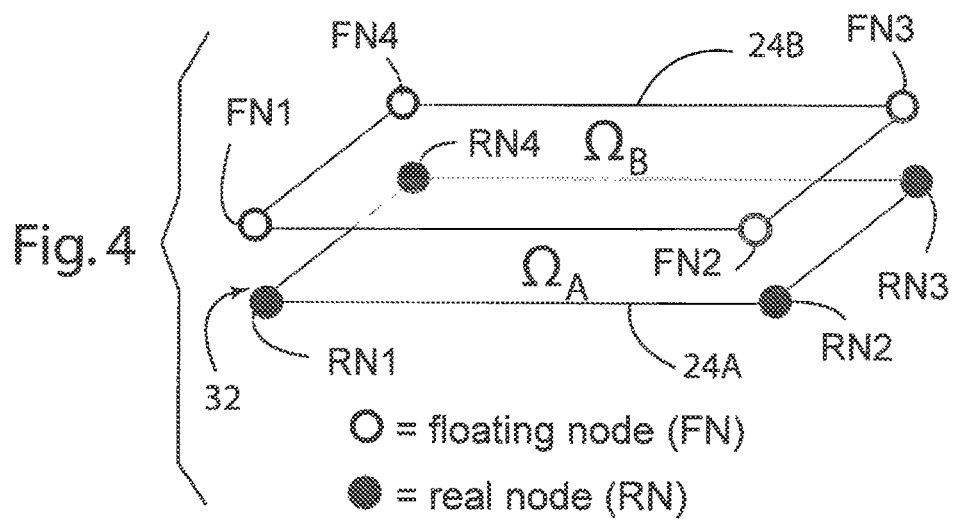
FIG. 4 is a schematic view of a split shell element corresponding to delaminations in a composite material.

With further reference to FIG. 4, the shell element 24 can be split into first and second overlapping shell elements or components 24A and 24B. Shell element 24A includes real nodes RN1-RN4, and the shell element 24B includes floating nodes FN1-FN4. The stiffness matrix for the split elements 24A and 24B of FIG. 4 is as follows:

$$K^{(e)} = \begin{bmatrix} [K_{\Omega_A}^{(e)}]_{24 \times 24} & [0] \\ [0] & [K_{\Omega_A}^{(e)}]_{24 \times 24} \end{bmatrix}_{48 \times 48} \quad (6.0)$$

In general, the undamaged shell element 24 (FIG. 3) may have a stiffness matrix corresponding to a composite laminate including a plurality of layers of reinforcing fibers disposed at different orientations. The shell element 24 may be split to form the shell elements or components 24A and 24B (FIG. 4) to simulate a delamination between the shell elements 24A and 24B. The stiffnesses of the shell elements 24A and 24B correspond to the portions of a composite laminate disposed on either side of a delamination crack. Shell elements or components 24A and 24B may be considered to be separate elements or they may be considered to be separate parts or components of a single element.

Figure 5:
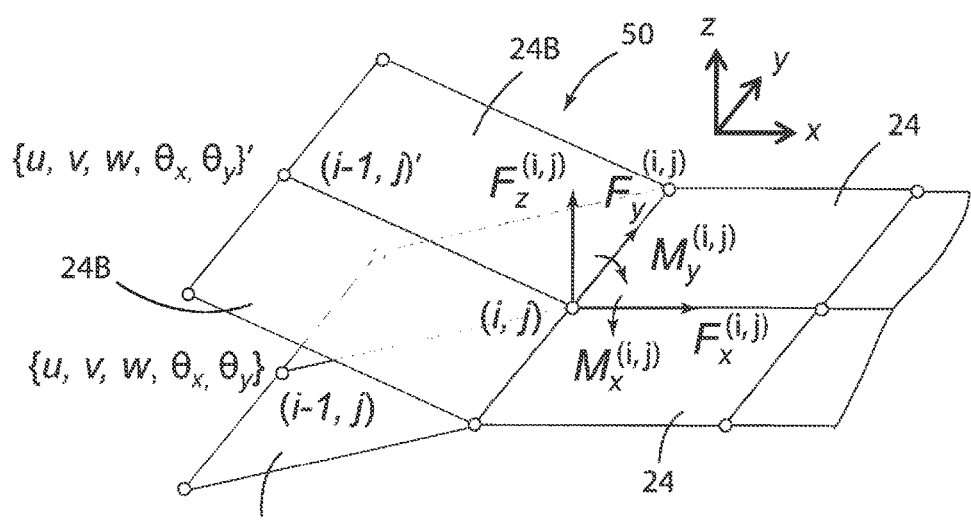
FIG. 5 is a schematic view showing coordinates and variables utilized in a Virtual Crack Closure Technique (VCCT)

With further reference to FIG. 5, a finite element model 50 may utilize the Virtual Crack Closure Technique (VCCT). Energy release rate equations originally given by Wang, J T, and Raju, I S. "Strain energy release rate formulas for skin-stiffener debond modeled with plate elements." *Engineering Fracture Mechanics* 54.2 (1996): 211-228, may be utilized. These equations are shown here corresponding to a delamination growth direction along the positive x direction as described in FIG. 5. Using delamination growth in the positive x-direction as an example, Mode I, Mode II, and total energy release rates at node (i,j) are determined as follows:

$$G_I^{(+x)} = \frac{-1}{2\Delta A^{(e)}} \left[ F_z^{(i,j)}\left(w^{(i-1,j)'} - w^{(i-1,j)}\right) + \right. \quad (7.0)$$
$$\left. M_x^{(i,j)}\left(\theta_x^{(i-1,j)'} - \theta_x^{(i-1,j)}\right) + M_y^{(i,j)}\left(\theta_y^{(i-1,j)'} - \theta_y^{(i-1,j)}\right) \right]$$

$$G_{II}^{(+x)} = \frac{-1}{2\Delta A^{(e)}} \left[ F_x^{(i,j)}\left(u^{(i-1,j)'} - u^{(i-1,j)}\right) \right] \quad (8.0)$$

$$G_T^{(+x)} = G_I^{(+x)} + G_{II}^{(+x)} \quad (9.0)$$

where F, M, w, u, and θ are nodal force, moment, z-displacement, x-displacement, and rotation, respectively. Nodal designations with a prime superscript refer to the "upper" set of elements (i.e., floating nodes) and crack extension area, $\Delta A^{(e)} = b^2$, is the area of an element for a square regular mesh. It will be understood that other mesh shapes may be utilized.

As described in Benzeggagh, M. L., M. Kenane. 1996. "Measurement of Mixed-Mode Delamination Fracture Toughness of Unidirectional Glass/Epoxy Composites with Mixed-Mode Bending Apparatus," *Composites Science and Technology*, 56(4):439-449, the mixed-mode critical energy release rate, $G_c$ may be calculated using the Benzeggagh-Kenane criterion as follows:

$$G_c^{(+x)} = G_{Ic} + (G_{IIc} - G_{Ic})(G_{II}^{(+x)}/G_T^{(+x)})^{nBK} \quad (10.0)$$

A summary of the VCCT is disclosed in Kreuger, "Virtual crack closure technique: History, approach, and applications, Applied Mechanics Review," supra. Thus, a detailed description of the VCCT is not believed to be required.

Figure 6:
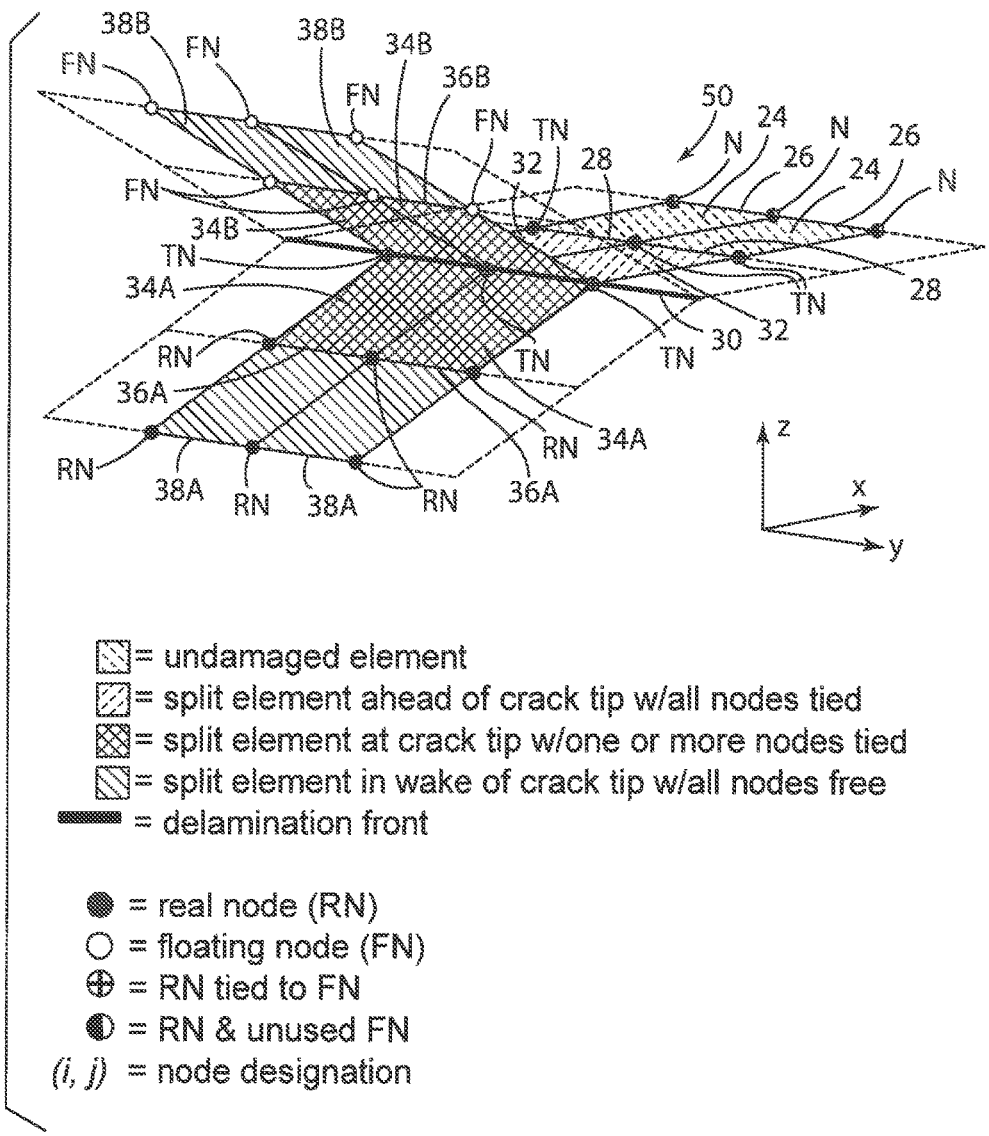
FIG. 6 is a schematic view showing implementation of a Virtual Crack Closure Technique (VCCT) showing opposing nodes tied together according to element state in relation to a crack tip or delamination front.

With further reference to FIG. 6, the enriched shell element 24 can be used in a mesh to represent four different damage states. These are illustrated in FIG. 6 and consist of 1) undamaged element, 2) split element ahead of the crack tip with all nodes tied, 3) split element at the crack tip with one or more nodes free, and 4) split element in the crack wake with all nodes free. At the end of every solution increment, VCCT is used on each delamination front tied node to determine if the tie should remain in place or be released resulting in a change in the adjacent element damage states (see Orifici, A. C., R. S. Thomson, R. Degenhardt, S. Busing, J. Bayandor. 2007. "Development of a Finite Element Methodology for Modelling Mixed-mode Delamination Growth in Composite Structures," 12$^{th}$ *Australian International Aerospace Congress, Australia*). Thus, the Virtual Crack Closure Technique (VCCT) may be used at a delamination crack tip or delamination front 30 utilizing tied nodes TN. The tied nodes TN comprise real nodes RN that are tied to floating nodes FN. One method to tie nodes together is by inserting high stiffness terms into the stiffness matrix coupling translational degrees of freedom. The undamaged elements 24 as labeled in FIG. 6, preceding the delamination crack tip or front 30 include nodes N that utilize real nodes RN only. Split elements 32 immediately preceding crack tip or front 30 include nodes TN at each corner of the split elements 32. As discussed above, each TN comprises a real node RN that is tied to a floating node FN. Alternatively, more than one row of split elements with all nodes tied may be defined ahead of a delamination to improve model accuracy and mesh independence.

The split elements include lower and upper element components 34A and 34B, respectively. The lower components 34A and upper components 34B adjacent to the "open" side of delamination crack tip or front 30 include tied nodes TN at the crack tip 30. The components 34A include real nodes RN along boundaries 36A away from the crack tip 30, and the components 34B include floating nodes FN along boundaries 36B away from the crack tip 30. The split components 38A and 38B away from the crack tip 30 include floating nodes FN and real nodes RN that are all free/not tied. In general, an offset is applied to the elements 24A, 24B, etc. that have been split coupling certain rotational and membrane degrees of freedom to account for the offset of the material on each side of a delamination from the original undamaged element's neutral axis. When using the FNM, opposing components such as 34A and 34B, are actually the same element with two separate regions or components.

An example of a VCCT is disclosed in Krueger, "Virtual crack closure technique: History, approach, and applications, Applied Mechanics Review," supra. Thus, a detailed description of VCCT is not believed to be required.

Figure 7:
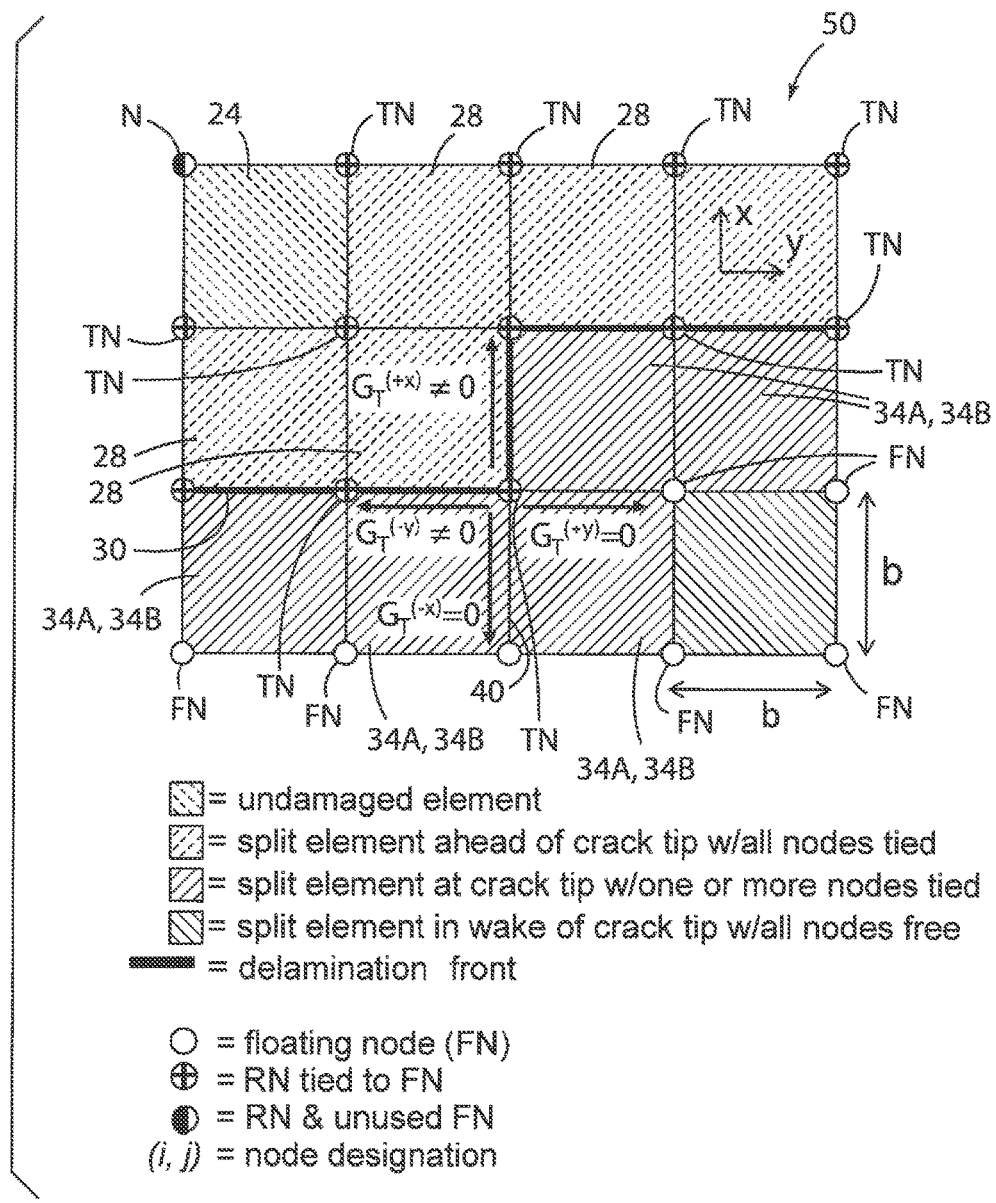
FIG. 7 is a schematic view showing an evaluation of delamination propagation in a finite element model.

With further reference to FIG. 7, a finite element model 50 similar to the model 50 of FIG. 6 but with a staggered delamination front is shown in plan view. Delamination propagation is evaluated, as show in FIG. 7, along directions X and Y aligned with the mesh. The total energy release rate ($G_T$) is calculated along the mesh lines or boundaries 40 in four directions at each tied node TN on a delamination front. If the total energy release rate ($G_T$) in any of the four propagation directions is greater than the critical energy release rate ($G_C$), the tie is released.

Although the propagation of a delamination crack may be determined utilizing the VCCT approach as described previously and as shown in FIGS. 6 and 7, it will be understood that other VCCT approaches such as described in Xie, D., S. B. Biggers Jr. "Strain energy release rate calculation for a moving delamination front of arbitrary shape based on the virtual crack closure technique. Part I: Formulation and validation," Engineering Fracture Mechanics, 2006, 73:771-785 or a Cohesive Zone (CZ) approach as described in Wisnom, M R, "Modelling discrete failure in composites with interface elements," Composites: Part A, 2010, 41:795-805 may also be utilized.

Figure 8:
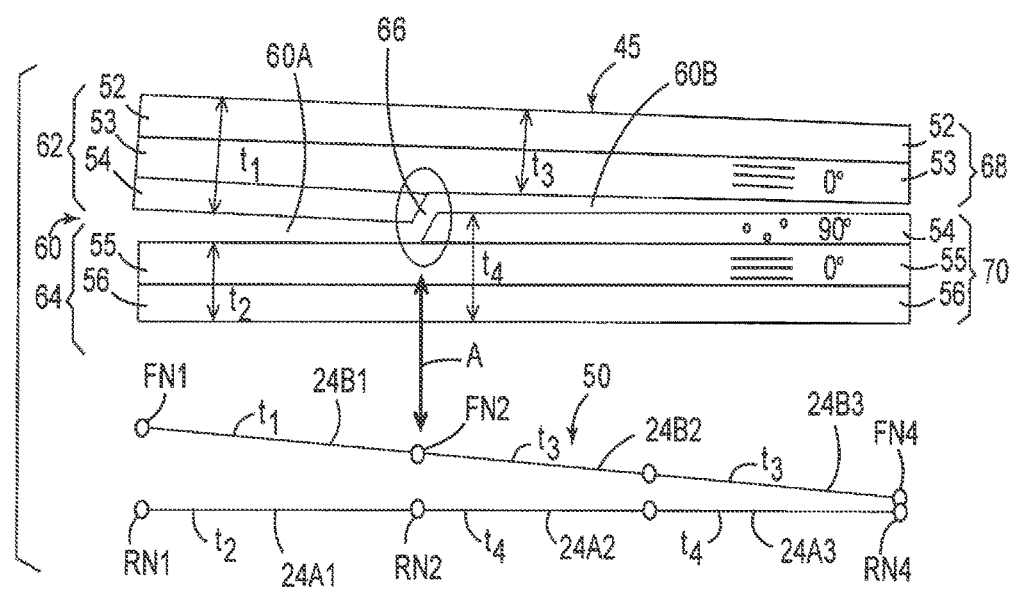
FIG. 8 is a schematic view including a physical schematic of delamination migration that has occurred and a corresponding representation in a shell element model where a stiffness discontinuity at an element boundary corresponds to a matrix crack in the physical schematic.

With further reference to FIG. 8, a laminate 45 may comprise a plurality of layers of fibers 52-56. The fibers may be oriented at 0° and 90° as shown in FIG. 8, or in other orientations as required for a particular application. A delamination crack 60 may include a first portion 60A with layers 52-54 disposed above the first crack portion 60A, and layers 55-56 disposed below the first crack portion 60A, forming a first laminate portion 62 having a thickness $t_1$, and a second laminate portion 64 having a thickness $t_2$. The delamination 60 may migrate via a matrix crack 66 from the first portion or interface 60A to a second delamination crack portion or interface 60B. Upper laminate portion 68 (layers 52 and 53) has a thickness $t_3$ above the new crack portion or interface 60B, and a lower portion 70 (layers 54-56) below the new crack or interface 60B has a thickness $t_4$.

As shown by the arrow A, nodes FN2 and RN2 of finite element model 50 correspond to the matrix crack 66 location. The matrix crack 66 is represented by a discontinuity corresponding to the integration of the stiffness matrix (equation 3.0, supra) across different thicknesses domains as follows:

$$K_{\Omega_A}{}^{(e)} = \iint_{A^{(e)}} H_{\Omega_A}{}^T [\int_{-h/2}^{z'} C(A,B,D,G)_{\Omega_A} dz] H_{\Omega_A} dA \quad (11.0)$$

$$K_{\Omega_B}{}^{(e)} = \iint_{A^{(e)}} H_{\Omega_B}{}^T [\int_{z'}^{-h/2} C(A,B,D,G)_{\Omega_B} dz] H_{\Omega_B} dA \quad (12.0)$$

where z' is the location of a delamination along the z-axis in a laminate.

Thus, the element 24B1 (thickness $t_1$) will have a stiffness corresponding to the layers 52-54. The element 24A1 (thickness $t_2$) has a stiffness matrix corresponding to the layers 55 and 56. However, the element 24B2 (formed after crack 60 migrates to the new interface 60B) has a thickness $t_3$ corresponding to layers 52 and 53. Element 24A2 has a thickness $t_4$ corresponding to layers 54-56.

Figure 9:
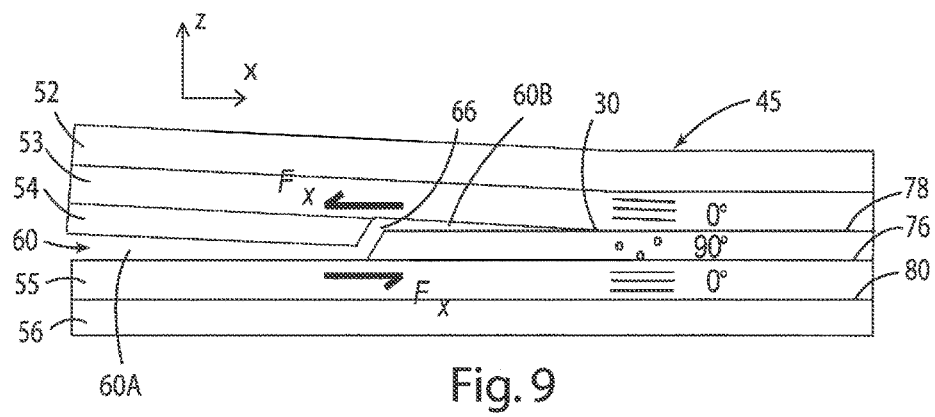
FIG. 9 is a schematic view showing delamination that has migrated in a composite laminate.

With further reference to FIG. 9, in the illustrated example delamination 60 propagates via a matrix crack from a first interface 76 (crack 60A) between layers 54 and 55 to a second interface 78 (crack 60B) between layers 53 and 54. However, the matrix crack 66 may also propagate in the opposite direction from interface 76 to a third interface 80 between layers 55 and 56. The direction of the propagation of matrix crack 66 may be determined utilizing the direction (sign, positive or negative) of the tie shear forces $F_x$ at the crack tip or delamination front 30. The shear force sign indicates the orientation of microcracks, or cusps, that precede the delamination 60. The tendency of propagation in the Z coordinate (FIG. 9) transverse to the present interface, i.e., up or down, may be determined by determining if the fiber orientation in the adjacent ply in the direction the cusps are pointing towards (i.e., the bounding fiber orientation) is such that the cusps are arrested or allowed to pass through as described in more detail in De Carvalho, N V, Chen, B Y, Pinho, S T, Ratcliffe, J G, Baiz, P M, Tay, T E. 2015, "Modeling delamination migration in cross-ply tape laminates," *Composite: Part A* 71:192-203.

Figure 10:
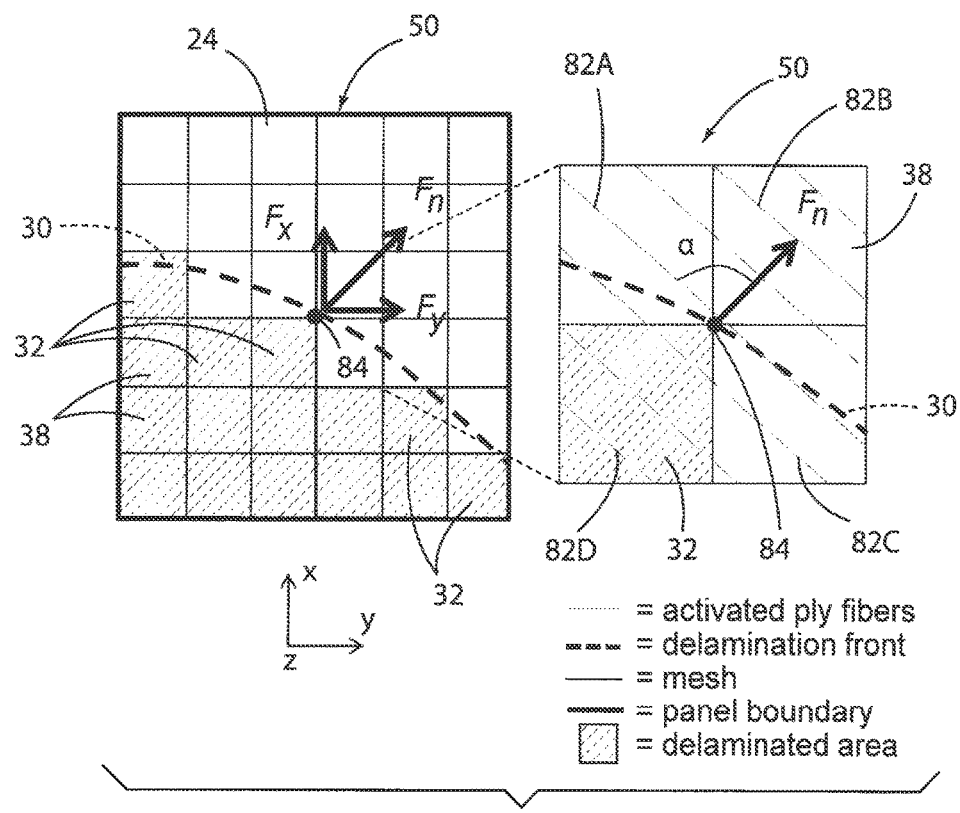
FIG. 10 is a schematic view showing cusp orientation and adjacent fiber orientation.

With further reference to FIG. 10, another aspect of the present invention involves determining the cusp orientation about the Z axis as discussed in Canturri, C., E. S., Greenhalgh, S. T. Pinho, J. Ankersen, 2013, "Delamination growth directionality and the subsequent migration process: The key to damage tolerant design, Composites Part A: Applied Science and Manufacturing," (54):79-87 relative to the bounding ply fibers. The crack 60 may have a three dimensional crack tip or delamination front 30 with a physical representation shown in dashed lines in FIG. 10 superimposed over the staggered approximation made in the mesh. At a given node 84 located on delamination front 30, the angle of the force vector $F_n$ is calculated from the individual tie shear forces $F_x$ and $F_y$ acting on node 84. The cusp orientation about the Z-axis may be assumed to be orthogonal to $F_n$. The relative angle, α, between $F_n$ and the bounding fiber orientation may be used as the basis for a criterion determining if cusps are allowed to pass through and result in a delamination migration. If the conditions for described above are met, migration still may not occur if the cusps are greatly misaligned with the direction of delamination growth and/or the tie shear forces are small (i.e., possible in a Mode I dominated delamination).

Figure 11:
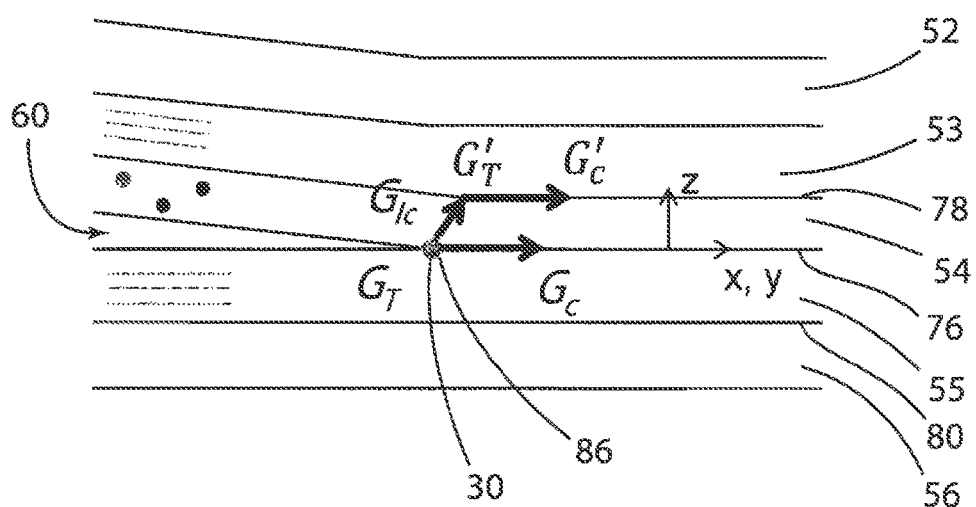
FIG. 11 is a physical schematic view showing one potential delamination-migration energy criteria for use in a shell element model.

With further reference to FIG. 11, energy criteria can be utilized to determine migration and/or delamination at a delamination front 30. At delamination front 30, the total energy release rate ($G_T$) is calculated. The critical energy release rate ($G_C$) is calculated for the first interface 76. The total energy release rate and critical energy release rate (designated $G'_T$ and $G'_C$ in FIG. 11 at interface 78) are assumed to be very similar (or identical) to those of the current interface. A critical energy release rate is given by the equation 10.0 (supra).

$G_{IC}$ is the Mode I critical energy release rate, wherein Mode I is a crack that is "opening." $G_{IIC}$ is the Mode II critical energy release rate, wherein Mode II is a shear or "sliding" type crack. $G_{II}$ is the Mode TI energy release rate. The following assumptions are utilized:

$$G_{I_C}^{(fiber)} = \infty$$

$$\Delta U_{mig} << \Delta U_{delam}$$

Were $\Delta U_{mig}$ is the energy dissipated due a matrix crack (i.e. migration), and $\Delta U_{delam}$ is the energy dissipation due to growth of the delamination crack 60.

The energy release rates and critical energy release rates can be utilized to predict one of three possibilities at a delamination front node 86. In the following, $G_{Ic}$ refers to matrix crack (i.e., cusp) critical energy release rate and $G_c$ refers to delamination critical energy release rate. $G_T$ is compared to both toughness quantities in a manner similar to De Carvalho, N V, Chen, B Y, Pinho, S T, Ratcliffe, J G, Baiz, P M, Tay, T E. 2015, "Modeling delamination migration in cross-ply tape laminates," *Composite: Part A* 71:192-203. Specifically, migration and delamination occur if:

$$G_T > G_{Ic}$$

&

$$G_T > G_c$$

Delamination occurs if:

$$G_T < G_{Ic}$$

&

$$G_T > G_c$$

No growth occurs if:

$$G_T < G_c$$

Referring again to FIG. 1, the steps designated 16 and 18 may utilize the delamination/migration criteria discussed above in connection with FIG. 11. The cusp orientation is determined using the tie shear forces as discussed above in connection with FIGS. 10 and 11. As discussed above in connection with FIG. 8, the matrix crack is modeled utilizing a discontinuity in the mesh stiffness at opposing element boundaries. Alternatively, matrix cracks may be inserted into the mesh by using floating nodes to break nodal connectivity between adjacent elements that represent a single ply.

Referring again to FIG. 1, the splitting of elements either at a new migrated interface (designated 20 in FIG. 1) and/or splitting the next element in the direction of growth at the current interface (designated 22 in FIG. 1) utilize adaptive fidelity (i.e. splitting elements on demand as needed, but not otherwise). It will be understood that this approach permits modeling of crack growth without the need to provide a large number of parallel/overlapping elements corresponding to the individual layers of the composite material at the time the initial finite element model is created.

Initially separate delaminations in a finite element model may grow independently but at some point in a solution procedure the initially separate delaminations may reach a common nodal location in the mesh. Or, similarly, separate deliminations may be adjacent to one another during growth. The migration criteria as described previously or a similar variation may be applied in these instances to determine if the delaminations link together via a matrix crack and whether a TN is released or the tie is maintained. Furthermore, if separate delaminations exist at different interfaces, the delaminations may grow to a common location in the mesh or they may be adjacent to one another during growth. The migration criteria as described above can be used to determine how elements are split and which ties are released, if any, in the region where the two delaminations interact.

The simulation tool may optionally include a fiber failure simulation capability. One method of doing this is use of continuum damage mechanics as described in Matzenmiller, A. J. Lubliner, R. L. Taylor, 1995, "A constitutive model for anisotropic damage in fiber-composites," *Mechanics of Materials*, (20)2:125-152.

All references contained herein are hereby incorporated by reference in their entirety.

What is claimed is:

1. A computerized method of simulating damage growth in composite laminates having a plurality of interfaces between adjacent layers of fibers disposed in a matrix material and at least one delamination crack having a delamination front at a current interface, the method comprising:

forming a finite element model of a composite material by providing a plurality of nodes and an associated single layer of elements comprising shell or plate finite elements, wherein the elements comprise stiffness matrices corresponding to a plurality of layers of fibers disposed in a matrix material;

storing the finite element model in computer memory;

using a computer to determine a finite element solution to the finite element model subjected to a load;

providing separate current stiffness matrices corresponding to laminate layers on each side of a delamination crack at the current interface;

utilizing predefined criteria to determine if the delamination crack grows as a result of a most recent incremental finite element load step solution as part of a finite element model solution for an applied load;

if the delamination crack does grow, predicting the spatial orientation of microcracks that precede the delamination front and evaluating if an adjacent layer of fibers arrests the microcracks to thereby determine if the delamination front remains at the current interface or migrates in a direction that is transverse to the elements through at least one of the adjacent layers of fibers via a matrix crack to a new interface;

if the delamination crack grows and remains at the current interface, split one or more adjacent elements in the direction of growth into new separate stiffness matrices that are the same as the current stiffness matrices whereby the new separate stiffness matrices correspond to laminate layers on each side of the delamination crack at its current interface;

if the delamination grows and migrates to a new interface that is offset from the current interface, split one or more adjacent elements in the direction of growth into new separate stiffness matrices that are modified relative to the current stiffness matrices and correspond to the new interface location that is offset from the current interface to thereby account for migration of the delamination to the new interface.

2. The method of claim 1, wherein:

forming a finite element model includes forming a plurality of floating nodes for each single layer shell or plate element.

3. The method of claim 2, wherein:

the separate stiffness matrices are formed utilizing the floating nodes.

4. The method of claim 1, including;

forming tied nodes at the delamination front;

predicting the spatial orientation of microcracks that precede the delamination front utilizing tie forces at the tied nodes.

5. The method of claim 4, including:

utilizing tie forces of the tied nodes to predict if an adjacent layer of fibers arrests the microcracks; and splitting one or more adjacent elements in the direction of growth at the new interface if an adjacent layer of fibers does not arrest the microcracks.

6. The method of claim 1, wherein:

if the delamination crack grows according to a first delamination growth prediction at the current interface or a new interface, the interface location of the adjacent element that is determined to be split is superseded by a second delamination growth prediction that has also determined the adjacent element to be split but at a different interface if the second delamination growth prediction is energetically dominant.

7. The method of claim 1, including:

using a computer to determine at each load step if a new delamination crack forms according to a predefined damage initiation criteria.

8. The method of claim 1, wherein:

the finite element model includes a plurality of delamination cracks; and including:

forming separate stiffness matrices corresponding to the laminate layers on each side of each delamination crack.

9. The method of claim 8, including:

utilizing predefined criteria to determine if the delamination cracks grow at a current interface corresponding to each delamination crack as a result of a most recent finite element solution to an applied load.

10. The method of claim 1, wherein:

the differences in the stiffness matrices define a stiffness discontinuity at a boundary between adjacent shell elements and thereby model a matrix crack.

11. A computerized method of simulating damage growth in composite laminates having a plurality of interfaces between adjacent layers of fibers disposed in a matrix material, the method comprising:

forming a finite element model of a composite material, the finite element model comprising a plurality of nodes and having a region having a single layer of shell or plate elements comprising a composite stiffness matrix corresponding to a plurality of layers of fibers disposed in a matrix material;

storing the finite element model in computer memory;

using a computer to determine a finite element solution to the finite element model subjected to a load;

if the finite element model has a delamination crack, providing separate stiffness matrices corresponding to laminate layers on each side of the delamination crack;

predicting the spatial orientation of microcracks that precede the delamination front to thereby determine if the delamination front migrates via a matrix crack to a new interface;

if the delamination migrates to a new interface, split one or more adjacent shell elements in the direction of growth to form new shell elements, the new shell elements having stiffness matrices that are modified from those of the current interface split location to correspond to a new interface location that is offset from the current interface to thereby account for migration of the delamination to the new interface by providing a stiffness discontinuity at a boundary between adjacent shell elements thereby modeling the matrix crack.

12. The method of claim 11, including;

forming tied nodes at the delamination front;

predicting the spatial orientation of microcracks that precede the delamination front utilizing tie forces of the tied nodes.

13. The method of claim 12, including:

utilizing tie forces of the tied nodes to predict if an adjacent layer of fibers arrests the microcracks.

14. The method of claim 11, including:

utilizing predefined criteria to determine if the delamination crack grows at the current interface between adjacent layers of fibers as a result of a most recent incremental finite element load step solution as part of a finite element model solution for an applied load.

15. The method of claim 14, wherein:

if the delamination crack grows, with or without migration, the interface location of an adjacent element that is determined to be split may be superseded by another nearby element.

16. A computerized method of simulating damage growth in composite laminates having a plurality of interfaces between adjacent layers of fibers disposed in a matrix material, the method comprising:

forming a finite element model of a composite material, the finite element model comprising a plurality of nodes and having a region having a single layer of shell or plate elements comprising a composite stiffness matrix corresponding to a plurality of layers of fibers disposed in a matrix material;

storing the finite element model in computer memory;

using a computer to determine a finite element solution to the finite element model subjected to a load;

using a computer to evaluate at each load step in a numerical finite element solution procedure if a delamination crack exists in the finite element mesh and/or if a delamination crack forms according to a predefined damage initiation criteria;

if a delamination crack forms or is already present, determining the location in the laminate including a present interface;

if a delamination crack does not form, or if a delamination crack does not exist, repeat the step of determining a finite element solution;

if a delamination crack forms or already exists, providing separate stiffness matrices corresponding to laminate layers on each side of the delamination crack;

predicting the spatial orientation of microcracks that precede the delamination front and evaluating if an adjacent layer of fibers arrests the microcracks to thereby determine if the delamination front remains in the current interface or migrates in a direction that is traverse to the elements through at least one of the adjacent layers of fibers via a matrix crack to a new interface;

if the delamination grows and migrates to a new interface, split one or more adjacent shell elements to form new shell elements having stiffness matrices to thereby account for migration of the delamination to the new interface.

17. The method of claim 16, including:
providing a stiffness discontinuity at a boundary between adjacent shell elements thereby modeling the matrix crack.

18. The method of claim 16, including:
utilizing predefined criteria to determine if the delamination crack grows at the current interface between adjacent layers of fibers as a result of a most recent incremental finite element load step solution as part of a finite element model solution for an applied load.

19. The method of claim 18, including:
if the delamination crack grows and remains at the current interface, split one or more adjacent elements in the direction of growth into separate stiffness matrices corresponding to laminate layers on each side of the delamination crack at its current interface.

20. The method of claim 16, including,
forming tied nodes at the delamination front;
predicting the spatial orientation of microcracks that precede the delamination front utilizing tie forces of the tied nodes at a delamination front.

* * * * *